US011517926B2

United States Patent
Raykhfeld et al.

(10) Patent No.: US 11,517,926 B2
(45) Date of Patent: Dec. 6, 2022

(54) PRODUCT DELIVERY METHOD TO THE TREATMENT OBJECT AND THE DEVICE FOR ITS IMPLEMENTATION

(71) Applicant: ECO SHIELD ENGINEERING LLC, Eagan, MN (US)

(72) Inventors: Yevgeniy Raykhfeld, Eagan, MN (US); Igor Golenistsev, Eagan, MN (US)

(73) Assignee: ECO SHIELD ENGINEERING LLC, Eagan, MN (US)

( * ) Notice: Subject to any disclaimer, the term of this patent is extended or adjusted under 35 U.S.C. 154(b) by 0 days.

(21) Appl. No.: 16/096,688

(22) PCT Filed: Apr. 26, 2017

(86) PCT No.: PCT/US2017/029681
§ 371 (c)(1),
(2) Date: Oct. 25, 2018

(87) PCT Pub. No.: WO2017/189752
PCT Pub. Date: Nov. 2, 2017

(65) Prior Publication Data
US 2019/0320639 A1 Oct. 24, 2019

Related U.S. Application Data

(60) Provisional application No. 62/327,987, filed on Apr. 26, 2016, provisional application No. 62/327,679, filed on Apr. 26, 2016.

(51) Int. Cl.
*B05B 13/00* (2006.01)
*B05B 7/00* (2006.01)
(Continued)

(52) U.S. Cl.
CPC ......... *B05B 13/005* (2013.01); *A01M 7/0032* (2013.01); *B05B 7/0075* (2013.01); *B05B 17/06* (2013.01); *A61L 9/14* (2013.01)

(58) Field of Classification Search
CPC ....... B05B 7/0075; B05B 12/08; B05B 12/12; B05B 13/005; A01M 7/0032
See application file for complete search history.

(56) References Cited

U.S. PATENT DOCUMENTS 3,341,081 A * 9/1967 King ...................... B08B 3/028
222/146.4
3,698,644 A 10/1972 Nystuen
(Continued)

FOREIGN PATENT DOCUMENTS

| EP | 2581137 A1 | 4/2013 |
|---|---|---|
| GB | 1156259 A | 6/1969 |
| RU | 2262393 C1 | 10/2005 |

OTHER PUBLICATIONS

Farajollahi A, Healy SP, Unlu I, Gaugler R, Fonseca DM (2012) Effectiveness of Ultra-Low Volume Nighttime Applications of an Adulticide against Diurnal Aedes albopictus, a Critical Vector of Dengue and Chikungunya Viruses. PLoS ONE 7(11): e49181. doi:10.1371/journal.pone.0049181 (Year: 2012).*

(Continued)

*Primary Examiner* — Cody J Lieuwen
(74) *Attorney, Agent, or Firm* — Cozen O'Connor

(57) ABSTRACT

A fluid dispersion system and method used for spraying large areas with near-monodispersed, aerosolized fluid droplets. More specifically, the system creates and distributes a cloud of near-monodispersed droplets of fluid by pumping pressurized air and fluid through fluid dispersion machinery and into, and out of, a fluid dispersion nozzle. The fluid dispersion machinery is a combustion engine-driven air compressor system that includes an engine, radiator, fuel tank, fluid tank, fluid piping system, fluid pump, air compressor, air compression intake, one or more fluid dispersal nozzles, air ducting, clutch, and control system. The method of fluid dispersion is implemented at night during a night-
(Continued)

time air inversion when there is a temperature difference between the temperature of air at the top of an object and the temperature of air near the ground surface.

19 Claims, 11 Drawing Sheets

(51) Int. Cl.
*B05B 17/06* (2006.01)
*A01M 7/00* (2006.01)
*A61L 9/14* (2006.01)

(56) References Cited

U.S. PATENT DOCUMENTS

| | | | |
|---|---|---|---|
| 4,317,308 A | 3/1982 | Derrick et al. | |
| 4,992,206 A * | 2/1991 | Waldrop | B05B 7/10 239/403 |
| 5,248,448 A * | 9/1993 | Waldron | B05B 7/10 239/338 |
| 5,296,702 A | 3/1994 | Beck et al. | |
| 5,522,930 A | 6/1996 | Modera et al. | |
| 5,713,521 A | 2/1998 | Scheffel | |
| 6,203,186 B1 | 3/2001 | Cruz | |
| 8,655,559 B2 | 2/2014 | Peake et al. | |
| 2002/0030117 A1 * | 3/2002 | Bryan | A01M 13/00 239/61 |
| 2002/0100815 A1 * | 8/2002 | Doebler | A01M 7/0014 239/67 |
| 2006/0131348 A1 | 6/2006 | Gould et al. | |
| 2009/0025794 A1 * | 1/2009 | Dorendorf | A01M 7/0014 137/1 |
| 2016/0136672 A1 * | 5/2016 | Doswell | B05B 15/55 239/11 |
| 2018/0111148 A1 * | 4/2018 | Batcheller | A01M 7/0042 |

OTHER PUBLICATIONS

International Search Report for PCT/US2017/029681, dated Sep. 28, 2017, 4 pages.
International Search Report for PCT/US2017/029691, dated Jul. 27, 2017, 2 pages.
Written Opinion for PCT/US2017/029681, dated Sep. 28, 2017, 5 pages.
Written Opinion for PCT/US2017/029691, dated Jul. 27, 2017, 4 pages.
U.S. Appl. No. 16/096,689.
Enz, J.W., et al., "Air Temperature Inversions: Causes, Characteristics and Potential Effects on Pesticide Spray Drift", Article AE1705, 16 pages, 2014.
GRDC, Grains Research & Development Corporation, Surface Temperature Inversions and Spraying Fact Sheet, 4 pages, Reprinted Aug. 2013.
U.S. Appl. No. 16/096,689, filed Apr. 26, 2017.

* cited by examiner

PRODUCT DELIVERY METHOD TO THE TREATMENT OBJECT AND THE DEVICE FOR ITS IMPLEMENTATION

CROSS-REFERENCE TO RELATED APPLICATION

This application claims the benefit of U.S. Provisional Application No. 62/327,679 filed Apr. 26, 2016 and titled METHOD AND SYSTEM FOR FLUID DISPERSION, and claims the benefit of U.S. Provisional Application No. 62/327,987 filed Apr. 26, 2016 and titled FLUID DISPERSION NOZZLE, which, along with the subject matter disclosed in the U.S. Application filed the same date as the present application, Attorney Ref. ESE/0002USU1 and titled FLUID DISPERSION NOZZLE are hereby incorporated by reference, with such incorporation limited such that no subject matter is incorporated that is contrary to the explicit disclosure herein.

FIELD OF THE DISCLOSURE

The disclosed invention relates to a method and system for spraying and dispersing fluid over large areas of land. More specifically, the disclosed invention relates to a fluid dispersion system and method used to create and distribute a cloud of aerosolized, near-monodispersed droplets by pressurizing fluid and air via a fluid pump and air compressor in a fluid dispersion machine, pumping the pressurized air and fluid to a fluid dispersion nozzle, and using the pressurized air to redirect and collide the fluid particles with solid surfaces in the nozzle to create aerosolized droplets prior to dispersing the aerosolized droplets over an agricultural field, open fields, forests, or enclosed structures.

BACKGROUND OF THE INVENTION

There are several situations, both outdoor and indoor, in which a fluid needs to be sprayed over large areas. For example, spraying is currently used to protect agricultural and forestry activities, to control wild plants for zero tillage farming, to control psychoactive plants, to manage pests in insecticidal processing or other environments where pest control is desired, to apply fertilizer to plants' leaves, to deliver fertilizer through stalks and leaves, to desiccate plants, to treat plants with fungicides, to manage mosquito and vector disease, and other broad-range applications.

However, current dispersers are limited in the range in which they can reach and the method of fluid application to the plants. Additionally, they unevenly cover the land being sprayed, waste the fluid being dispersed, and create environmental hazards through, for example, runoff of excess chemicals. Therefore, a fluid dispersion system and method is needed that is capable of spraying and dispersing fluid materials evenly, over longer distances, and without unnecessary chemical waste.

SUMMARY OF THE INVENTION

The present disclosure is a fluid dispersion system and method used for spraying large areas of agricultural land with polydispersed or near-monodispersed, aerosolized fluid droplets. More specifically, the system creates and distributes a cloud of polydispersed or near-monodispersed droplets of fluid by pumping pressurized air and fluid through fluid dispersion machinery and into, and out of, a fluid dispersion nozzle. The fluid dispersion machinery is a combustion engine-driven air compressor system that includes an engine, radiator, fuel tank, fluid tank, fluid piping system, fluid pump, air compressor, air compression intake, one or more fluid dispersal nozzles, air ducting, clutch, and control system.

DETAILED DESCRIPTION

Figure 1:
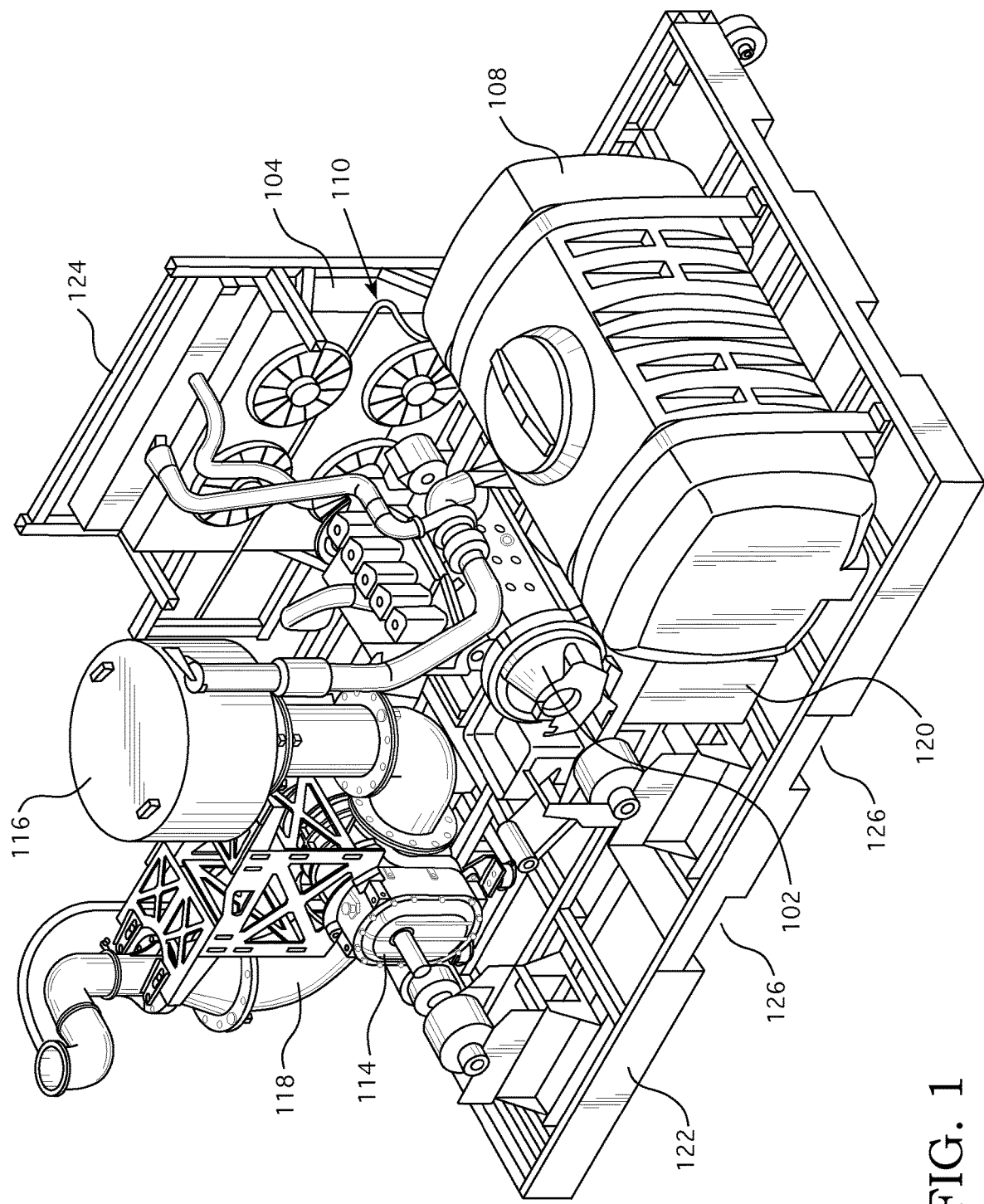
FIG. 1 is a perspective view of fluid dispersion machinery according to one embodiment of the disclosed invention.

The present disclosure relates to a fluid dispersion system and method used to create and distribute a cloud of polydispersed or near-monodispersed droplets of fluid. Various embodiments of the fluid dispersion system will be described in detail with reference to the drawings, wherein like reference numerals represent like parts and assemblies throughout the several views. Reference to various embodiments does not limit the scope of the fluid dispersion system disclosed herein. Additionally, any examples set forth in this specification are not intended to be limiting and merely set forth some of the many possible embodiments for the fluid dispersion system. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

The disclosed system is comprised of a fluid dispersion system and method, wherein a fluid dispersion machine accelerates fluid and air particles, a fluid dispersion nozzle aerosolizes the fluid particles to create near-monodispersed droplets by combining the fluid particles with the accelerated air particles, and a novel method is implemented to ensure accurate distribution of the near-monodispersed droplets. More specifically, these features function together to combine fluid materials with pressurized air, which results in the aerosolization of the fluid and enables the aerosolized fluid particles to travel long distances. For example, in a preferred embodiment, the fluid may exit the nozzle in five to 150 micron wide droplets and may be capable of traveling up to two miles.

In addition to the fluid dispersion machine and nozzle, the following disclosure includes a method of dispersing fluids that is dependent on the devices disclosed herein. The design of the fluid dispersion system, as well as the design of the method, enables dispersion of a polydisperse or near-monodisperse aerosol, use of wide-range nozzles, and a high aerosol flow range based on the parameters of the air fed to the nozzle. The dispersion results are obtained by eliminating cluttering of the air and fluid flow in the nozzle by, for example, maintaining consistent fluid pressure in the nozzle.

The practical use of the invention will allow for efficient and quality fluid dispersion by creating an aerosol of the required droplets size that can travel extended distances (for example, up to two miles) and be affected by temperature inversions.

Method

The fluid is sprayed by creating a cloud of polydispersed or near-monodispersed droplets of physiologically active agents in the atmosphere (for example, the troposphere). The fluid that is sprayed can be fertilizer, fungicides, herbicides, insecticides, disinfectants, or other chemical, biological, and mineral-based significant fluids. The same components and processes can be used to disperse any fluid regardless of the density and viscosity of the fluid. Due to the fine particle size created by the disclosed nozzle and system, the fluid can travel extremely far distances. In some embodiments, after the fluid exits the fluid dispersion system, it is in the form of polydispersed or near-monodispersed droplets (for example, droplets with diameters between five and 150 microns). In other embodiments, the fluid exits the fluid dispersion system in the form of monodispersed droplets. This dispersion method results in less fluid being used compared to pre-existing fluid dispersion systems, which lessens the impact of active chemicals on the environment and decreases costs associated with situations and settings where fluid dispersion is typically used. For example, fluid dispersion is frequently used for maintenance of plants and animals in an agricultural setting, for forest protection, for treatment of indoor structures, and for vector disease control. All of these scenarios could benefit from the disclosed system and method of fluid dispersion.

While the current disclosure primarily describes use of the machine and method in a plant-growing context, the same machines and methods may be implemented in livestock equipment and premises, forest protection, indoor treatment of structures, and vector disease control. In this context, the chemicals used may be disinfectants and the use of disinfectants with the disclosed machine and methods may also result in the benefit of more effective application of chemicals to desired surfaces.

Generally, the method of fluid dispersion is comprised of fluid flow from a fluid pump 112, airflow from an air compressor 114, acceleration of airflow in a nozzle, and combination of the fluid and accelerated airflow in the nozzle resulting in an aerosol. The aerosol's dispersion can be adjusted by changing the discharge rates of the fluid.

While the discharge rates of the fluid and air may be adjusted, in a preferred embodiment, the pressure of the fluid flow is maintained at a constant rate. Further, the maximum flow rate can be maintained within a specified range regardless of the preset range of the flow amount. For example, when the fluid flow rate increases from the fluid dispersion machine to the fluid dispersion nozzle, the fluid flow pressure is maintained by increasing the fluid flow rate out of the nozzle. More specifically, the decrease in the specific energy of the aerosol dispersion due to an increase in fluid flow rate to the nozzle is compensated by an increase in fluid flow rate out of the nozzle.

The method of fluid dispersion out of the nozzle is comprised of: (1) injecting fluid at a high pressure through the center of the nozzle; (2) allowing the fluid to hit various barriers that breaks the fluid particles into smaller, polydispersed or near-monodispersed particles; and (3) combining the polydispersed or near-monodispersed droplets with air flowing through the nozzle, wherein the air pushes the polydispersed or near-monodispersed droplets forward away from the nozzle and permits the polydispersed or near mono-dispersed droplets to be carried by the air and wind as a cloud for an extended distance (for example, hundreds or thousands of yards).

While typical fluid dispersion methods for agricultural fields involve spraying the fluid during the day and pushing the fluid down onto the plant using gravitational forces, the disclosed method involves spraying the fluid during the night and allowing gravitational forces and natural temperature inversions to pull the cloud down onto the plant. More specifically, because of the minute size of the fluid particles, the fluid droplets can effectively travel for miles. Therefore, to control for placement of the fluid droplets over agricultural fields, the dispersion process ideally takes place at night when there is a very small, constant wind speed (between 0 miles per hour and 9 miles per hour) that can carry the fluid droplets for a limited amount of time before they are pulled onto the plants.

Therefore, to accurately disperse fluids using the disclosed method, the process of spraying is best employed at night, when overnight cooling of surface air results in a nocturnal temperature inversion that is dissipated after sunrise by the warming of air near the ground. More specifically, at night, the air temperature near the ground is cooler than the air temperature near the top of a plant. When the air temperature near the top of the plant is warmer than the air temperature near the ground, the air near the top of the plant is pulled down toward the ground.

Accordingly, when the aerosolized cloud of fluid or near-monodispersed droplets are ejected by the disclosed nozzle and hovering in the air near the tops of plants, the natural air inversion process will pull the fluid, in the form of aerosol or near-monodispersed droplets, down and cover the remainder of the plant. This process will result in minimal, if any, chemical residue making it to the ground, thereby ensuring a decrease in harm to the environment compared to current dispersion methods. It is important that minimal chemical residue ends up in the soil, as a preferred embodiment of the disclosed system involves the use of highly concentrated chemicals with minimal water used to dilute those chemicals. For example, one solution may include the use of only 10% water.

For ideal application to plants, the difference in air temperature between the top of the plant and the air near the ground is a crucial factor. Therefore, before activating the fluid dispersion system, a user should track the air temperature near the ground and the air temperature near the top of a plant and wait for a predetermined temperature difference between the air near the ground and the air near the top of the plant. Once the difference between the two positions meets that predetermined temperature difference (for example, approximately one degree Fahrenheit), with the air near the top of the plant being warmer, fluid dispersion through the nozzle and accompanying system should be initiated.

Due to the ease with which the aerosolized droplets can move through the air, application of the chemicals or other fluids to a field, forest, or enclosed structure during times when there is a wind may require a user to rotate the nozzle so it is distributing the aerosolized cloud in the direction of the wind (i.e., the near-monodispsersed droplets are released upwind). Therefore, if the wind is blowing in southwest direction, the user should line up the equipment on the north side of the field and drive from east to west with the nozzle facing in a southern or southwestern direction. If the wind is blowing in a southeast direction, the user should line up the equipment on the north side of the field and drive from west to east with the nozzle facing in a southern or southeastern direction. In addition to the cardinal direction that the nozzle is facing, it may also be angled higher than the top of the field to enable the aerosolized cloud to drift over the field instead of into it.

In some cases, the method of fluid dispersion is altered slightly for application of chemicals to trees and forests. More specifically, whereas application in an agricultural context ideally has the nozzle aimed at an angle above the field to compliment wind or air movement, application in a forestry context ideally has the nozzle aimed directly at the part of the tree or trees to which contact with the chemical is desired.

Fluid Dispersion Nozzle

Figure 12:
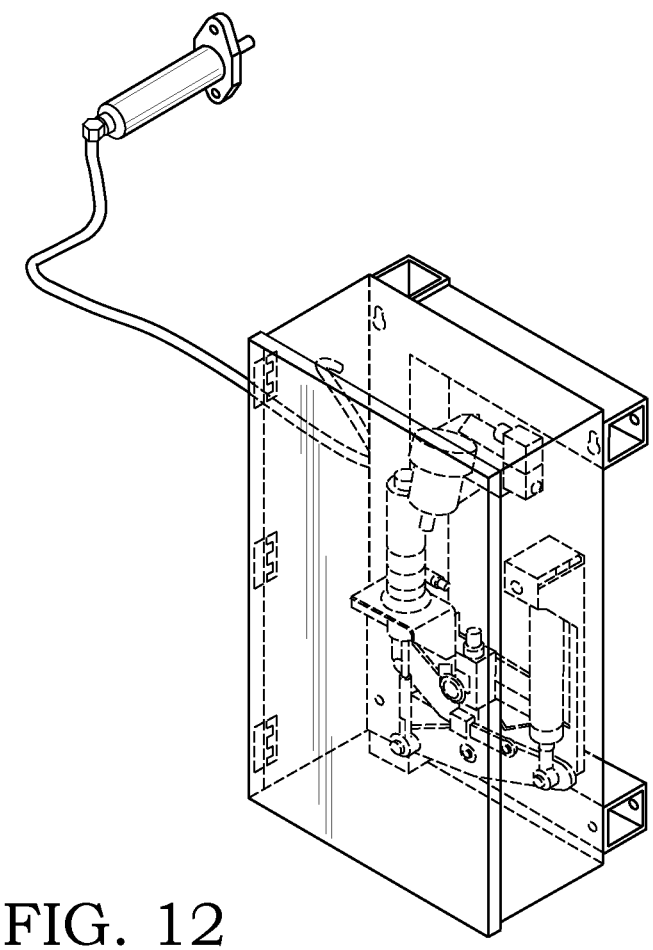
FIG. 12 illustrates a clutch actuator assembly of the fluid dispersion machinery according to one embodiment of the disclosed invention.
Figure 13:
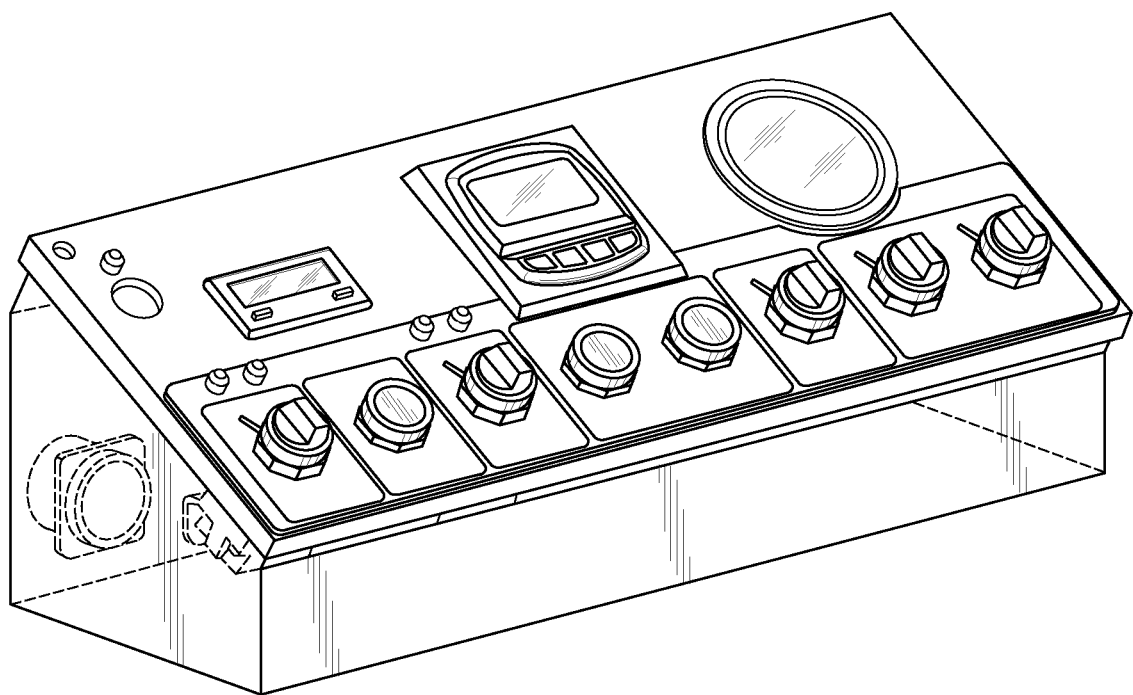
FIG. 13 illustrates a control system for a fluid dispersion system according to one embodiment of the disclosed invention.
Figure 14:
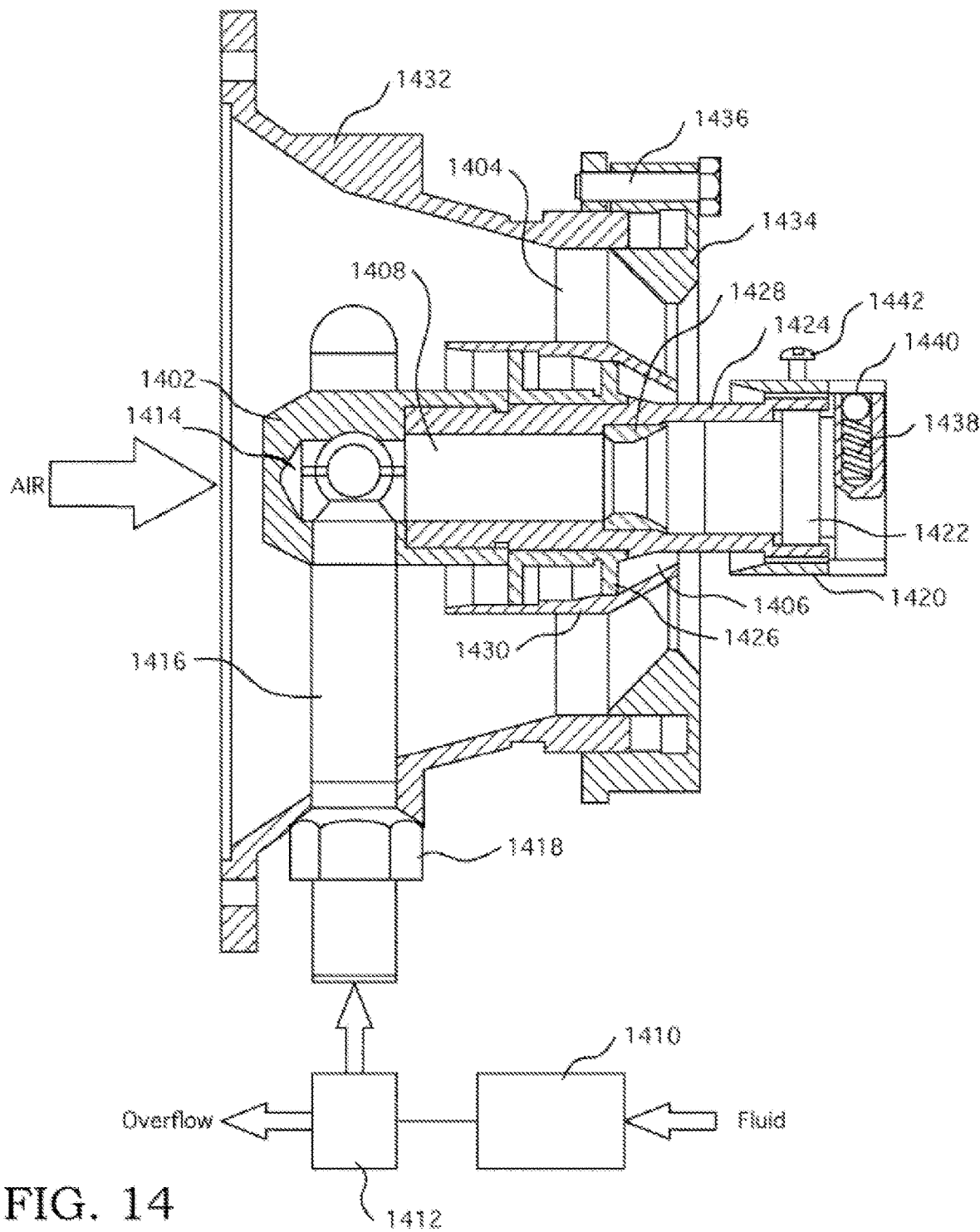
FIG. 14 is a side cross-sectional view of a fluid dispersion nozzle according to one embodiment of the disclosed invention.
Figure 15:
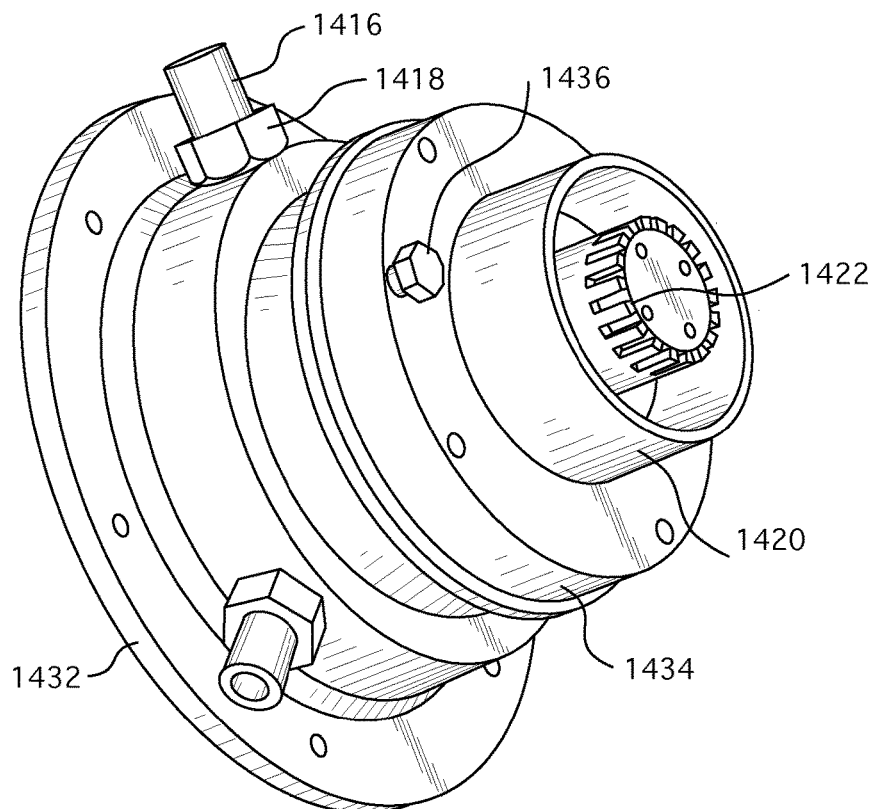
FIG. 15 is a front perspective view of the fluid dispersion nozzle of FIG. 14.
Figure 16:
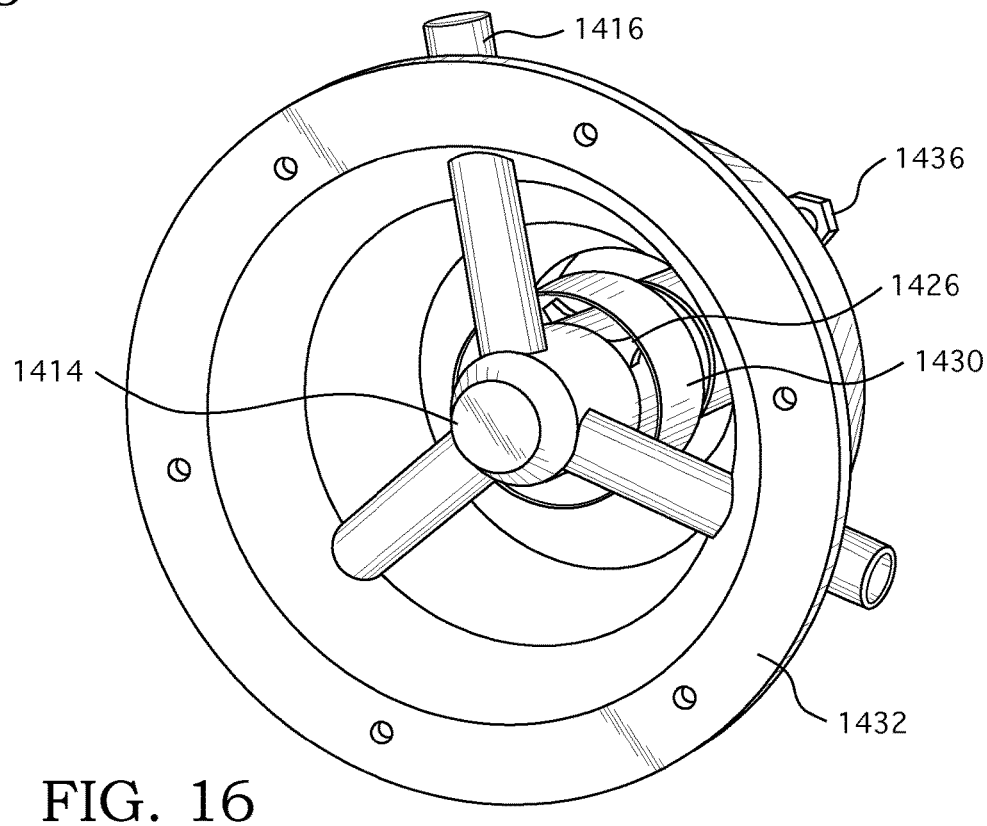
FIG. 16 is a rear perspective view of the nozzle of FIG. 14.
Figure 17:
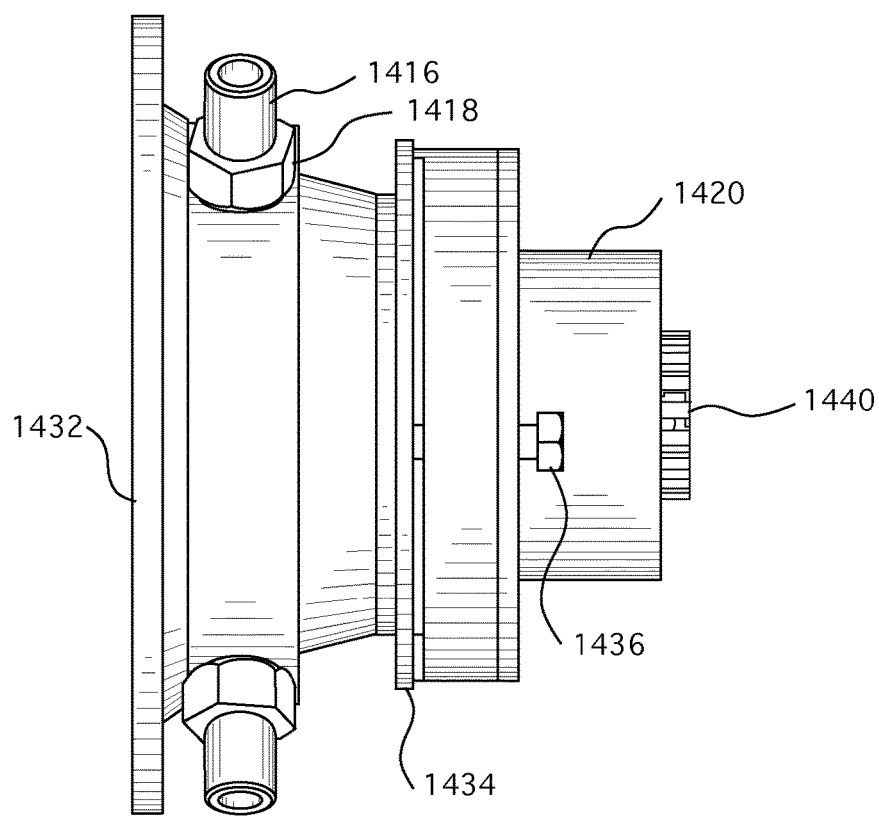
FIG. 17 is a side view of the nozzle of FIG. 14.
Figure 18:
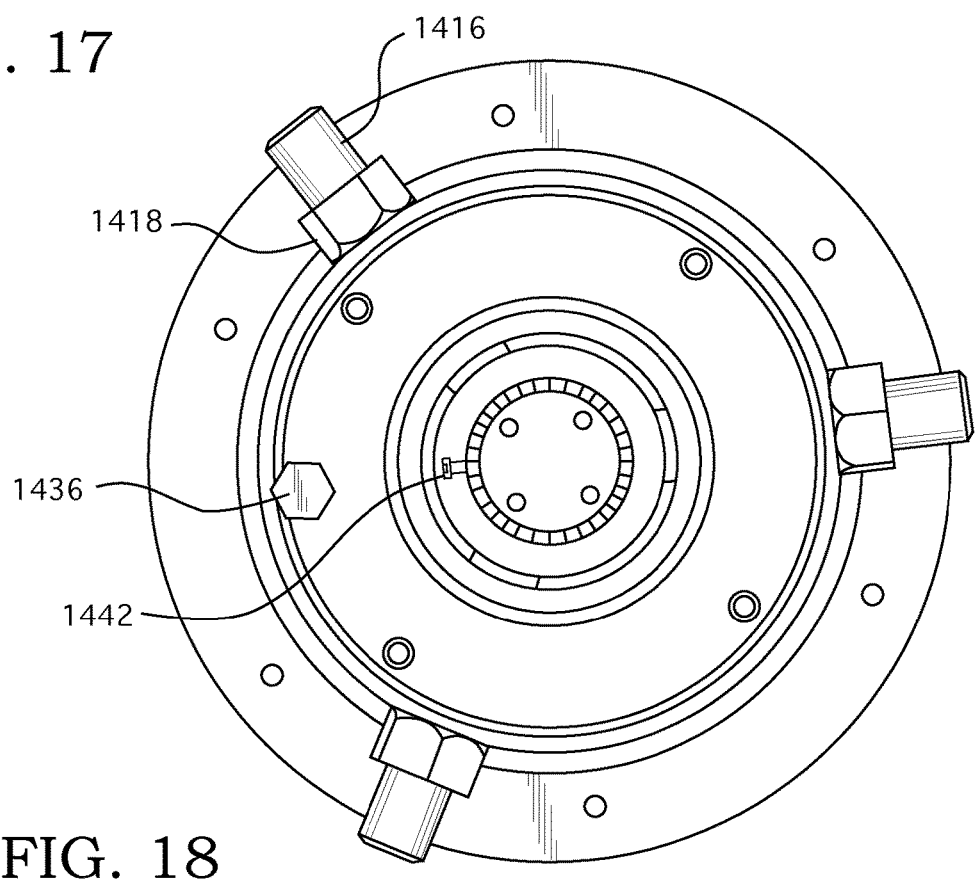
FIG. 18 is a front view of the nozzle of FIG. 14.

As briefly mentioned above, fluid travels through a fluid dispersion nozzle and is broken into smaller fluid droplets by physical impact with pressurized air and surfaces on the nozzle. In some embodiments, the nozzle is connected to fluid dispersion machinery, wherein the fluid dispersion machinery includes an engine 102, a fluid pump 112 that supplies pressurized fluid to the nozzle, an air compressor 114 that supplies pressurized air to the nozzle, and other components that help provide high velocity air and fluid to the nozzle. FIGS. 1-12 illustrate various features of the fluid dispersion machinery, and FIG. 13 illustrates one embodiment of a control system for the fluid dispersion system comprised of the fluid dispersion machinery and fluid dispersion nozzle. The combination of the machine, method, and the nozzle enable quality and highly efficient fluid dispersion over long distances with the highest possible degree of droplets' monodispersity.

Generally, the nozzle is a supersonic, adjustable, dual-contour nozzle connected to an air compressor 114 and a fluid pump 112, and is comprised of several components. The nozzle is designed to aerosolize the fluid from the fluid pump 112 by combining the fluid with ultrasound waves generated in the nozzle and enabling hydraulic fluid fragmentation of the fluid into droplets. The nozzle then blows the fluid aerosol out to the atmosphere in the form of a cloud. More specifically, initial pneumatic dispersion of the fluid droplets occurs using ultrasound air fluctuations, and the aerosol's final pneumatic dispersion is due to a supersonic air jet from of the nozzle, which supplies the aerosol to the site of application. The aerosol's dispersion is adjusted by discretely changing the airflow.

As described above, it is the combination of air and fluid that create the aerosolized, near-monodispersed droplets that are capable of traveling long distances. Therefore, the nozzle is dedicated to decreasing the size of the fluid particles and projecting them out from the nozzle using pressurized and accelerated air. The fluid dispersion machinery can use one or more permanent or interchangeable nozzles.

In a preferred embodiment, the nozzle, illustrated in FIGS. 14-18, is comprised generally of a nozzle body 1402 connected to the fluid dispersion machinery, two contours for airflow such as a main adjustable contour 1404 and an auxiliary contour 1406, an axial fluid injector 1408 for fluid flow, and a resonator 1420 for aerosolizing the fluid. The axial fluid injector 1408 is primarily contained within a hollow tip of the nozzle body 1414, which is centered in the nozzle and further connected to the fluid injector body 1424 and to the nose cone 1430 via the spacer 1426, which is centered accurately along the axis of the axial fluid injector 1408.

In some embodiments, fluid is initially pumped from a fluid tank 108 through a fluid pump 1410, through a pressure-regulating valve 1412, through a hollow pylon 1416 that is attached to the nozzle via a nut 1418, and into the hollow tip of the nozzle body 1414 that is one component of the axial fluid injector 1408. In some embodiments, the axial fluid injector 1408 can adjust the fluid flow. In some embodiments, there is one pylon 1416 through which fluid enters the axial fluid injector 1408. In other embodiments, there are a plurality of pylons 1416 (for example, three) through which fluid enters the axial fluid injector 1408. The pressure-regulating valve 1412 maintains the fluid pressure consistency of a predetermined rate. This rate maximizes the level of hydraulic energy, which maximizes the speed of the fluid from the axial fluid injector 1408.

In a preferred embodiment, once the fluid flows into the hollow tip of the nozzle body 1414 that is part of the axial fluid injector 1408, it progresses through at high velocity and comes into contact with a resonator 1420 and plunger 1422. The resonator 1420 is a high-speed resonator that redirects the fluid in order to decrease the size of the fluid particles. In some embodiments, the resonator 1420 has 14 to 36 axial slots interfaced with a metal ball-lock located in the plunger 1422. The resonator 1420 is attached to the fluid injector body 1424 from the outside via a threaded connection, such as screw 1442, and the plunger 1422 is attached to the fluid injector body 1424 from the inside via a threaded connection.

The plunger 1422 can be interfaced with a saddle 1428 on the conical surface of the contact type (for example: cone - torus). The interface of the plunger 1422 with the saddle 1428 ensures that the in-line, axial slot is opened accurately in the contact consistent with the conicity of the saddle 1428. In some embodiments, a ball 1440, such as a steel ball, can be pushed by a spring 1438 toward the outer wall of the resonator 1420 and can engage with each of the resonator's 14 to 36 axial slots. Therefore, the ball 1440 locks the plunger 1422 in place relative to the resonator 1420 each time the plunger 1422 is rotated and the ball 1440 lands between in-line slots. In some embodiments, when the plunger 1422 is turned by one slot relative to the resonator 1420, the in-line slot is opened at 0.0014---:-0.0022 mm, and when the plunger 1422 is turned by one revolution relative to the resonator 1420, the in-line slot is opened at 0.05---:-0.08 mm. A preferred embodiment of the disclosed invention involves activation of the nozzle when the ball 1440 is rotated through the first six axial slots.

When the fluid comes into contact with the resonator 1420 and plunger 1422, it hits the plunger 1422 and the fluid particles are reduced in size and are re-directed out of the axial fluid injector 1408 through a hole in the fluid injector body 1424. This hole, in some embodiments, is variable in size and controlled by rotation of the plunger 1422, as described above. After the fluid particles exit through the hole in the fluid injector body 1424, they come into contact with air flowing through the auxiliary contour 1406, are directed toward the resonator 1420, hit the resonator 1420, are reduced in size even further, are re-directed out of the resonator 1420, come into contact with air flowing through the main adjustable contour 1404, and are dispersed into the atmosphere as a monodisperse cloud. The fluid droplets are fragmented by the mechanical impact of the semi-fixed surfaces, which are vibrating with a forced ultrasound frequency of the fluid injector body 1424 and resonator 1420 that is caused by the impact of the ultrasonic air fluctuation.

As briefly mentioned above, the nozzle is a dual-contour nozzle that includes a main adjustable contour 1404 and an auxiliary contour 1406, both of which surround the axial fluid injector 1408, which is centered in the nozzle. The auxiliary contour 1406 is designed to aerosolize the fluid from the axial fluid injector 1408 by combining the fluid with ultrasound waves generated by airflow from the auxiliary contour 1406 to the resonator 1420. The main adjustable contour 1404 is designed for final fluid dispersion by using airflow through the main contour 1404 to blow the fluid aerosol out to the atmosphere in the form of a cloud. The main adjustable contour 1404 and the auxiliary contour 1406 have critical cross-sections that, in a preferred embodiment, are adjustable.

The main adjustable contour 1404 is, in some embodiments, defined as the space between the outer parts of the nozzle and the inner parts of the nozzle. More specifically, the outer parts of the nozzle that define the outer boundary of the main adjustable contour 1404 include the disperser body 1432 and the nozzle head 1434, which is held in place by a clamping screw 1436. The inner parts of the nozzle that define the inner boundary of the main adjustable contour 1404 include the hollow tip of the nozzle body 1414, the nose cone 1430, and the fluid injector body 1424.

The auxiliary contour 1406 is, in some embodiments, defined as the space between the axial fluid injector 1408 and the nose cone 1430, which is close-fitted on front and rear stationary blades of a spacer 1426. More specifically, the nose cone 1430 defines the outer boundary of the auxiliary contour 1406 and the hollow tip of the nozzle body 1414 and the fluid injector body 1424 defines the inner boundary of the auxiliary contour 1406.

As previously described, to aerosolize the fluid and disperse it over an agricultural field, the nozzle receives fluid and pressurized air and enables hydraulic fluid fragmentation of the fluid into droplets. More specifically, initial pneumatic dispersion of the fluid droplets occurs using ultrasound air fluctuations of the supersonic jet from the auxiliary contour 1406, and the aerosol's final pneumatic dispersion is due to a supersonic air jet from the main adjustable contour 1404 of the nozzle, which supplies the aerosol to the site of application. The aerosol's dispersion is adjusted by discretely changing the airflow from the auxiliary contour 1406 and from the main adjustable contour 1404.

In some embodiments, air enters from the back of the adjustable, dual-contour nozzle and is accelerated (for example, up to the speed of sound) through the main adjustable contour 1404 and the auxiliary contour 1406 due to a decrease in available volume and, therefore, a decrease in pressure. For example, the nozzle can be connected to an air compressor, which feeds the air to the nozzle under pressure, thereby enabling and ensuring a supercritical pressure differential in the nozzle.

As described above, it is the combination of air and fluid that create the aerosolized, monodisperse droplets capable of traveling long distances. Therefore, the nozzle is dedicated to decreasing the size of the fluid particles and projecting them out from the nozzle using pressurized and accelerated air.

Air flows through the auxiliary contour 1406 and combines with fluid that reflects off of the plunger 1422 and exits the axial fluid injector 1408. Due to the high velocity of air speed proceeding through the auxiliary contour 1406, the fluid that exits the axial fluid injector 1408 is redirected at high velocity into the resonator 1420 and reflected off of the resonator 1420. Therefore, the fluid droplets are dispersed into an aerosol by the pneumatic impact in the field of ultrasound air fluctuations of the supersonic jet from the auxiliary contour 1406, which is generated by the resonator 1420 and activated by a motor.

At the same time air is flowing through the auxiliary contour 1406, air is also flowing at high velocity through the main adjustable contour 1404. Due to the high velocity of air as it proceeds through the main adjustable contour 1404, the fluid that reflects off of the resonator 1420 combines with the air proceeding through the main adjustable contour 1404 and is dispersed into the atmosphere. Therefore, for the final pneumatic dispersion, the aerosol is directed to the supersonic air from the main adjustable contour 1404, where it receives the required dispersion and polydispersion rates. The aerosol is then fed by the supersonic air from the nozzle to the place of its application.

Aerosol dispersion, including polydispersion, is managed by smoothly changing the fluid flow by rotating the plunger 1422 and smoothly changing the air flow from the main adjustable contour 1404 by turning a nut. The multiplier impact of the hydraulic and pneumatic fragmentation of the fluid by combining the variables and individual impacts allows for adjusting the aerosol polydispersion level while keeping the dispersion rate unchanged.

Fluid Dispersion Machinery

As described above, the fluid dispersion nozzle receives fluid and air at high velocities from fluid dispersion machinery. Generally, the machinery in the support system is comprised of a combustion engine-driven fluid pump and air compressor that take fluid from a fluid reservoir and air from the atmosphere and pressurize the corresponding fluid and air before feeding them into the fluid dispersion nozzle. In some embodiments, the fluid dispersion machinery is capable of being transported and operated on a vehicle. For example, the machinery may be mounted in the open bed of a truck, enabling a user to drive the truck around or through an agricultural field, an open field, a forest, or an enclosed structure while employing the machinery and fluid dispersion nozzle. The machinery can interface with a remote control console, as illustrated in FIG. 12, that allows for control of engine speed and liquid injection flow as well as basic operational feedback. The remote control console can enable control from the cab of the transport truck.

Figure 2:
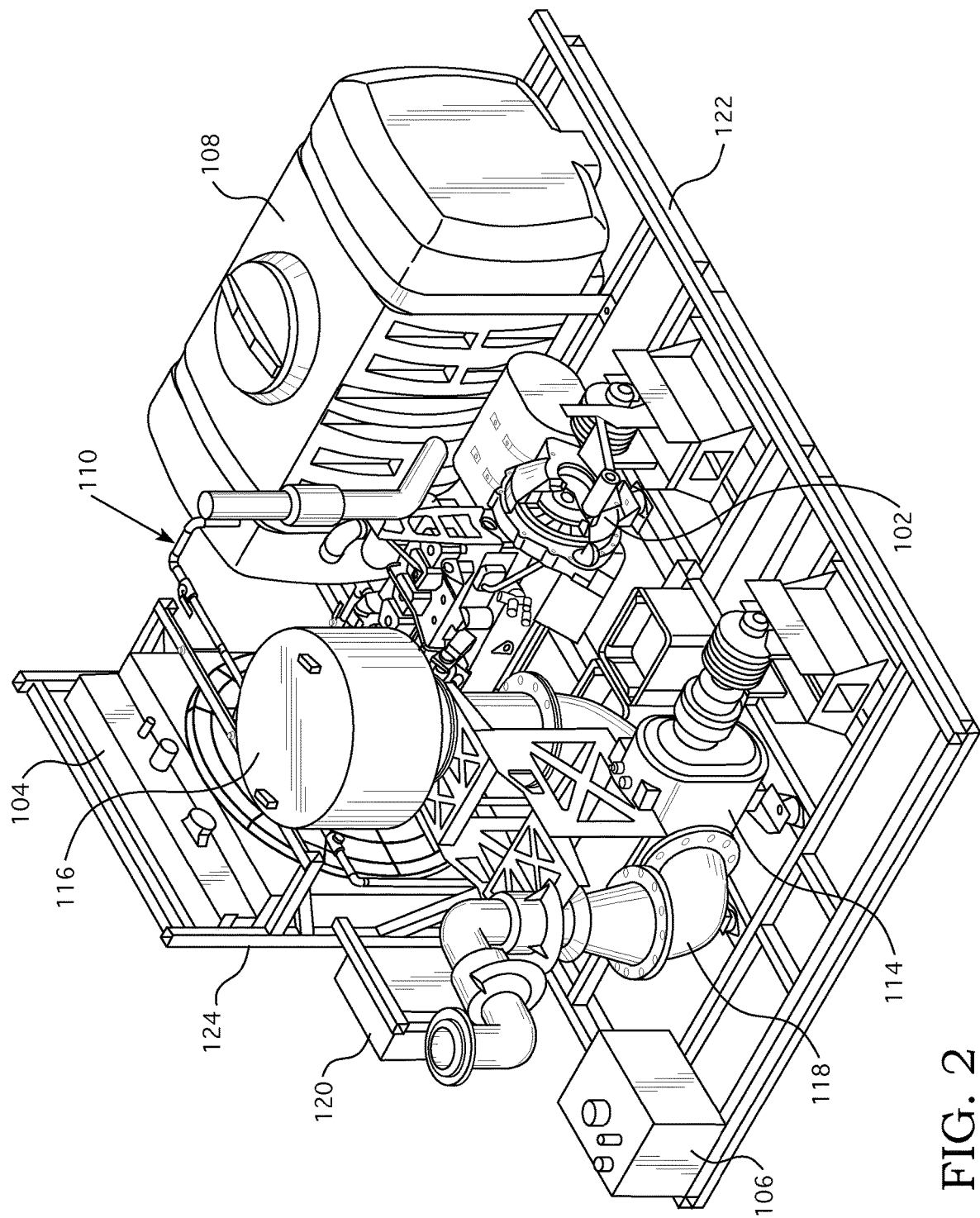
FIG. 2 is a perspective view of fluid dispersion machinery according to one embodiment of the disclosed invention.

Generally, the fluid dispersion machinery is comprised of an engine assembly, a clutch actuator assembly, a fluid system assembly that attaches to the nozzle or multiple nozzles, an air compression assembly that attaches to the nozzle or multiple nozzles, and rigid framing that the assemblies can mount or attach to. More specifically, as illustrated in FIGS. 1 and 2, the fluid dispersion machinery can include, but is not limited to, an engine 102 (for example: a diesel engine, a gas engine, a natural gas engine, a propane engine, or an electric motor), a radiator 104, a fuel tank 106, a fluid tank 108, a fluid piping system 110, a fluid pump 112, an air compressor 114, an air compression intake and silencer 116, air ducting 118, and a clutch 120 and can be controlled by an in-cab control system. In some embodiments, the machinery, except for the in-cab control system, can be attached to a base frame 122 and the engine 102 can be further (or alternatively) attached to a motor frame 124 that itself attaches to the base frame 122, thereby enabling easier movement of the fluid dispersion machinery on and off of the truck bed.

FIG. 1 illustrates a front left side perspective view of the fluid dispersion machinery according to one embodiment of the disclosed invention. FIG. 2 illustrates a back left side perspective view of the fluid dispersion machinery according to one embodiment of the disclosed invention. As mentioned above, specific parts of the fluid dispersion machinery, such as the fluid system assembly and the air compression assembly, attach to the fluid dispersion nozzle and provide fluid and air directly to the nozzle. In some embodiments, this attachment point is flexible and enables a user to rotate the direction that the nozzle faces. In other embodiments, the nozzle itself is the only part of the disclosed system that can rotate and the fluid dispersion machinery is fixed in place.

Figure 3:
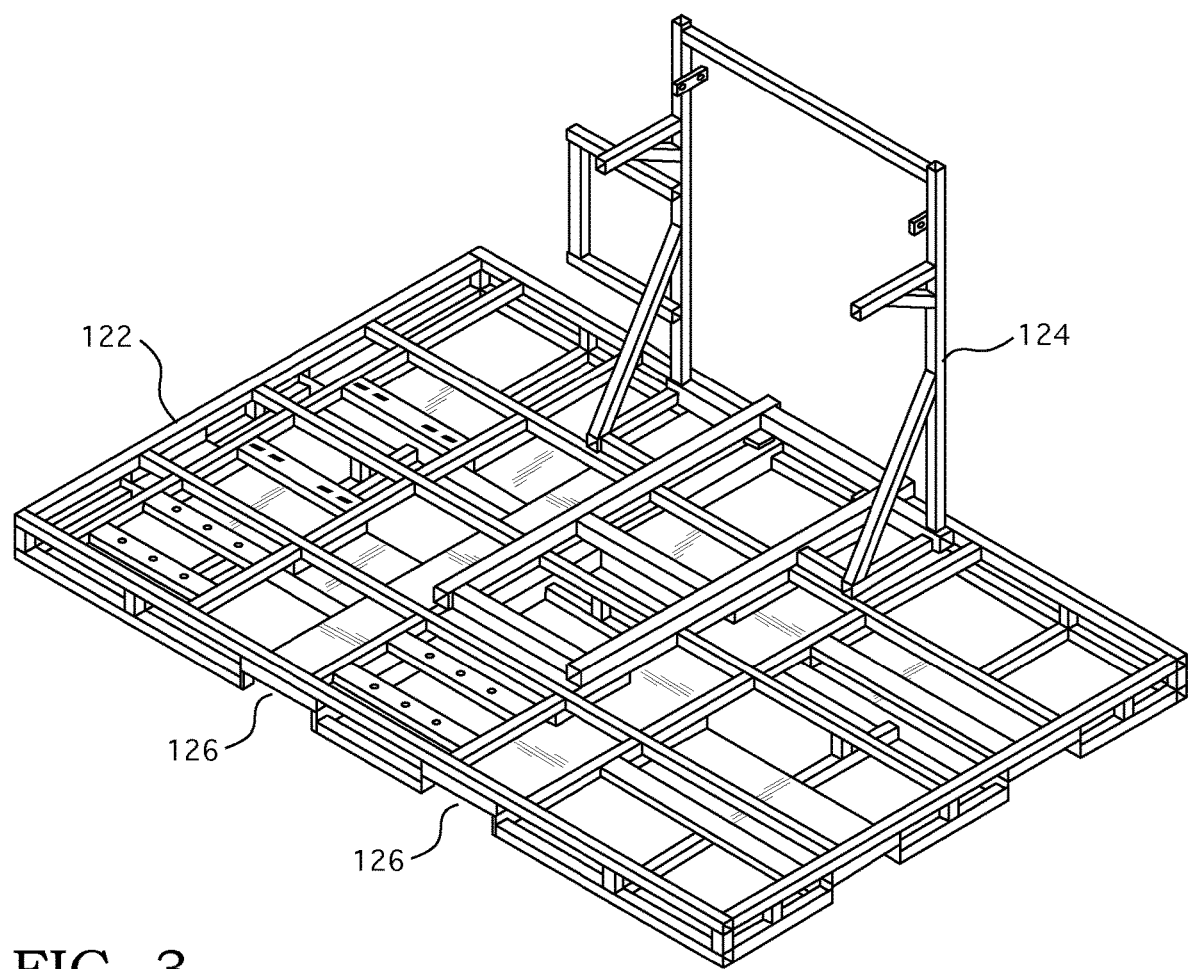
FIG. 3 illustrates a base frame and a motor frame of the of fluid dispersion machinery according to one embodiment of the disclosed invention.

A base frame 122 and motor frame 124, illustrated in FIG. 3, can provide attachment or mounting points for the rest of the machinery. In some embodiments, the motor frame 124 has a horizontal portion and a vertical portion that are configured at a 90-degree angle to each other. Therefore, when the motor frame 124 mounts onto the base frame 122, the horizontal portion of the motor frame 124 can mount to a central portion of the base frame 122, and the vertical portion of the motor frame 124 can mount to a right side of the base frame, as illustrated in FIG. 3. Additionally, the base frame 122 can have forklift access lifting points 126, which enable an individual to easily move the frames 122, 124 and the fluid dispersion machinery on and off of a truck bed or other elevated surface. The frames 122, 124 are rigid and can be made of metal such as, but not limited to, steel, stainless steel, aluminum, or any combination of these materials.

Figure 4:
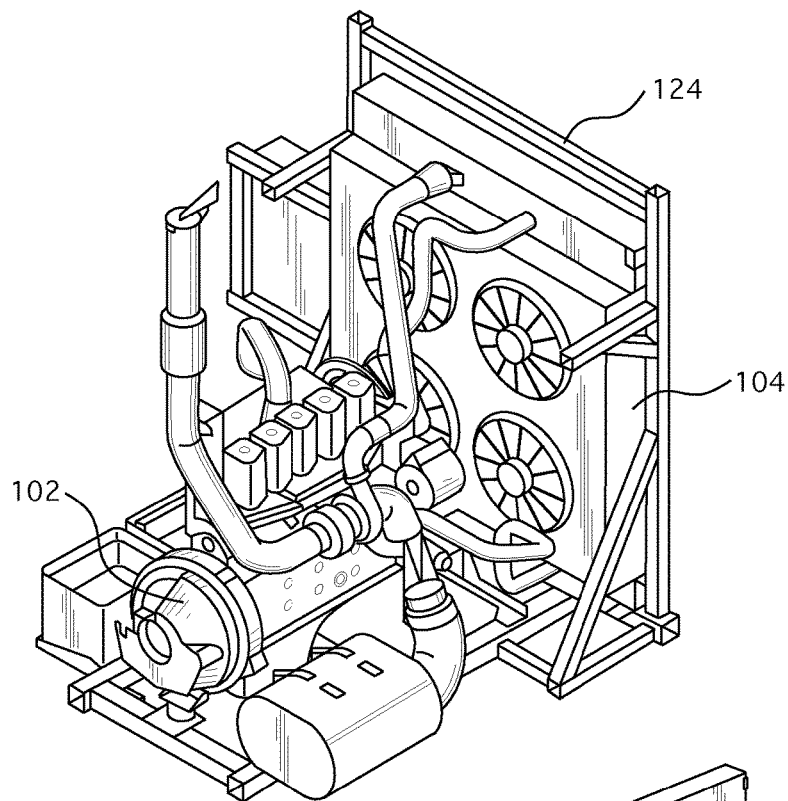
FIG. 4 illustrates a motor assembly of the fluid dispersion machinery according to one embodiment of the disclosed invention.
Figure 5:
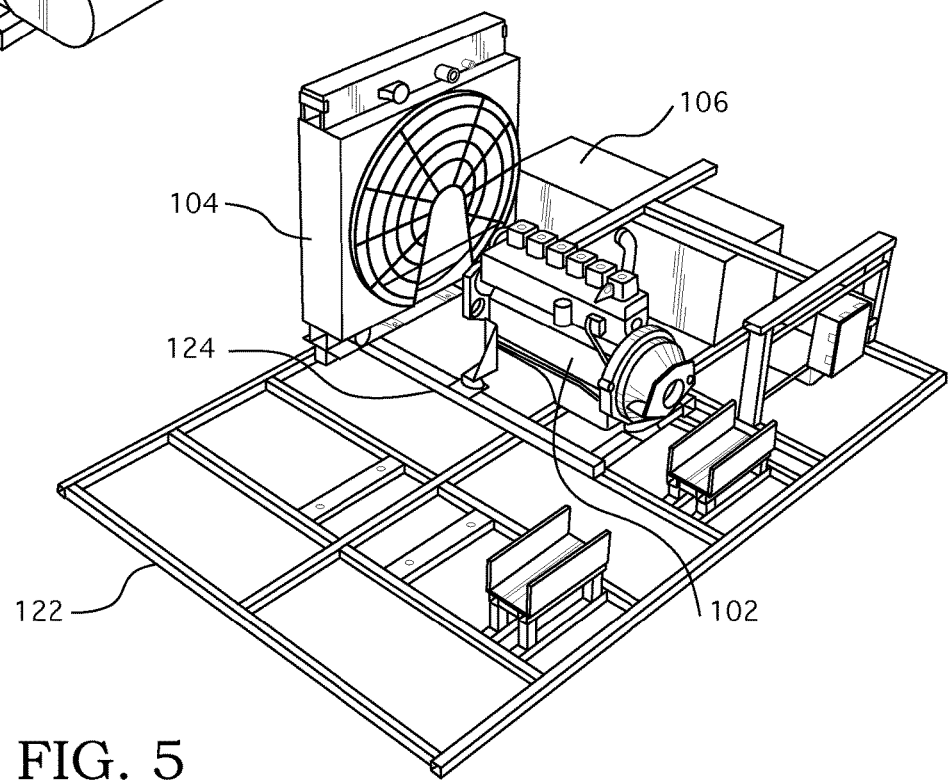
FIG. 5 illustrates the motor assembly of FIG. 4 mounted onto the base frame and motor frame of the fluid dispersion machinery according to one embodiment of the disclosed invention.
Figure 6:
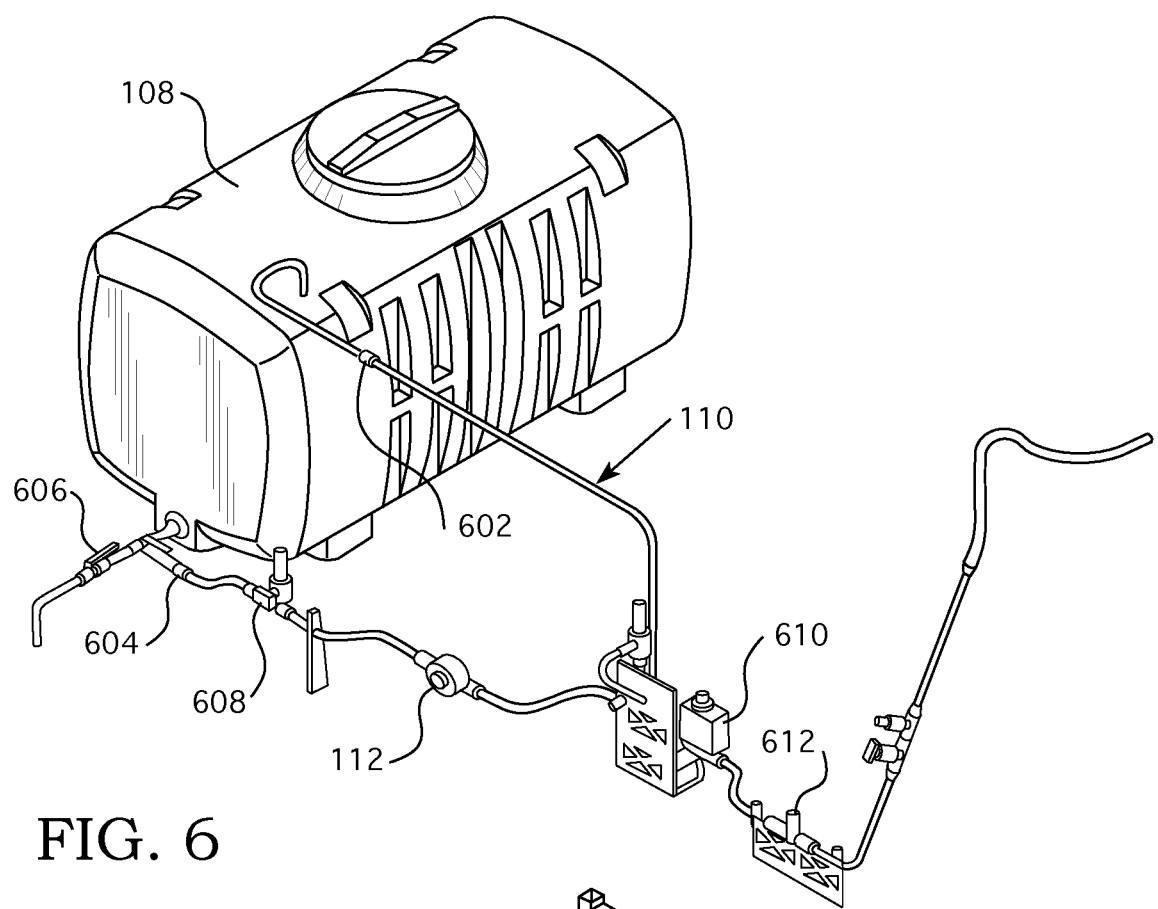
FIG. 6 illustrates a fluid system assembly of the fluid dispersion machinery according to one embodiment of the disclosed invention.
Figure 7:
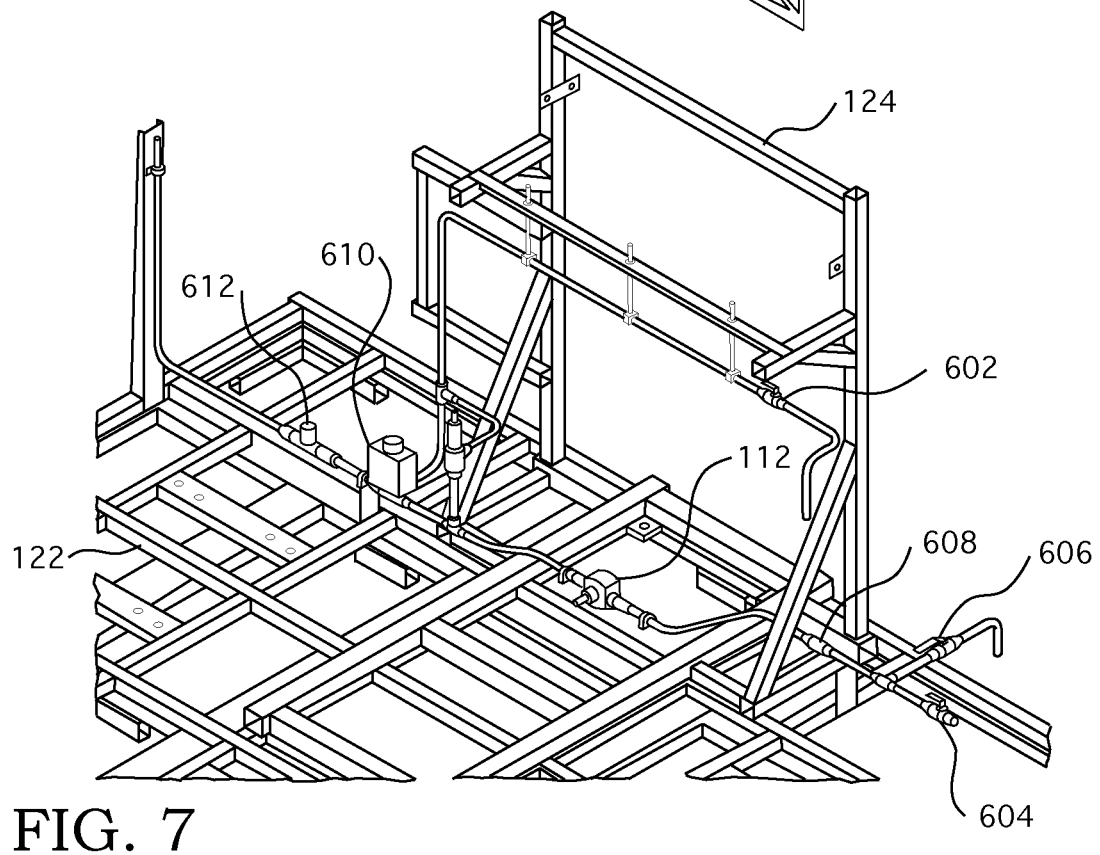
FIG. 7 illustrates a fluid piping system of the fluid system assembly of FIG. 6 mounted onto the base frame and motor frame of the fluid dispersion machinery according to one embodiment of the disclosed invention.
Figure 8:
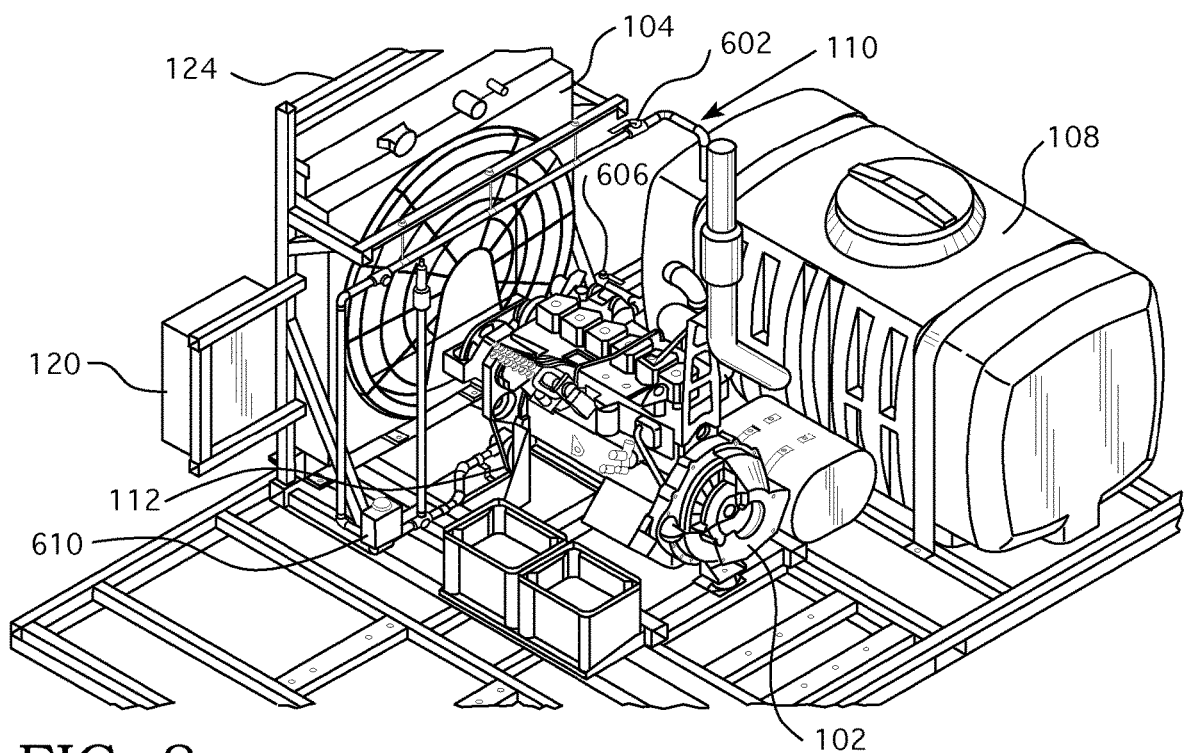
FIG. 8 illustrates the motor assembly of FIG. 4 and the fluid system assembly of FIG. 6 mounted onto the base frame and motor frame of the fluid dispersion machinery according to one embodiment of the disclosed invention.

In some embodiments, a portion of the fluid dispersion machinery includes an engine assembly comprised of an engine 102, such as a diesel engine, a radiator 104 to cool the engine 102, and a fuel tank 106 to hold fuel for the engine 102, as illustrated in FIGS. 4 and 5. FIG. 4 further illustrates one example of how the engine 102 and radiator 104 can mount onto the motor frame 124, wherein the engine 102 mounts to the horizontal portion of the motor frame 124 and the radiator 104 mounts to the vertical portion of the motor frame 124. FIG. 5 further illustrates one example of how the engine 102, radiator 104, and fuel tank 106 can mount onto the base frame 122. In some embodiments, the fuel tank 106 can be mounted elsewhere on the base frame 122, as illustrated in FIG. 2.

Figure 9:
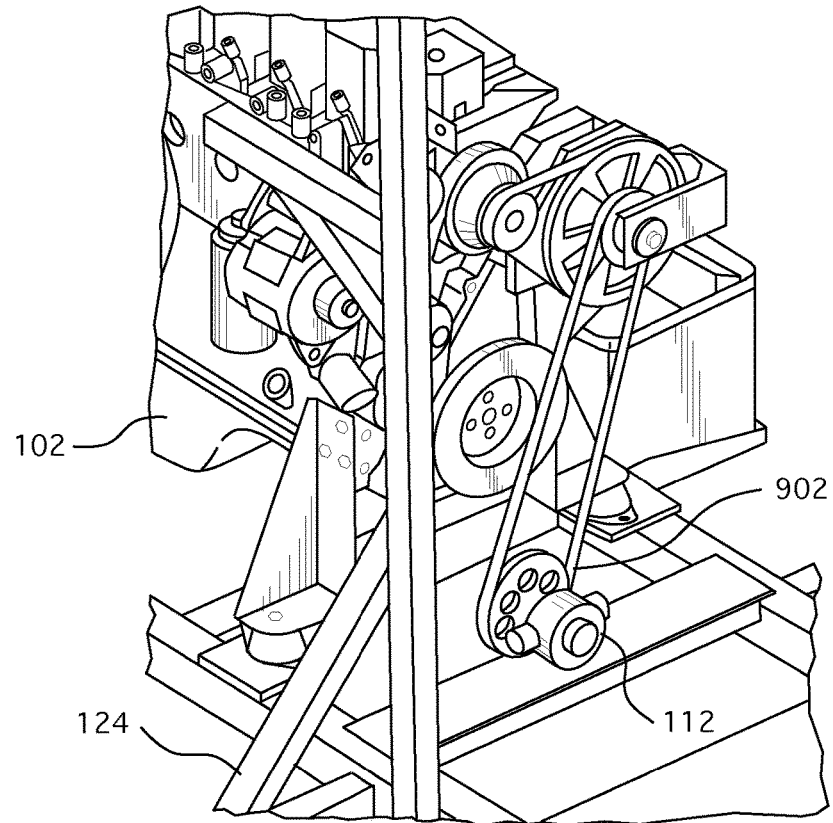
FIG. 9 illustrates a fluid pump attached to the motor of the fluid dispersion machinery system according to one embodiment of the disclosed invention.

The engine may have a range from 111.9 kW (150 HP) to 186.4 kW (250 HP) in order to support loads from the fluid pump 112, air compressor 114, a blower, and an alternator. The fuel tank 106 can have a level sender and, in a preferred embodiment, can support several hours (for example, at least eight) of runtime due to the critical timing involved in dispersion of the fluids. More specifically, because the fluids should be dispersed, in a preferred embodiment, during a temperature inversion and temperature inversions only happen for a limited period of time during the night hours, the engine 102 should have enough fuel to last it for that critical period of time. To engage or disengage the engine motor from the compressor 114, an individual can use a clutch 120. FIG. 12 illustrates one embodiment of a clutch actuator assembly that includes a clutch 120.

In some embodiments, a portion of the fluid dispersion machinery includes a fluid system assembly comprised of a fluid tank 108 for holding the fluid to be dispersed, a fluid piping system 110 for transporting fluid from the fluid tank 108 to the fluid dispersion nozzle, and a fluid pump 112 included in the fluid piping system 110 and run by the engine 102, as illustrated in FIGS. 6, 7, and 9. The fluid piping system 110 can include, in addition to the fluid pump 112, an upper tank valve 602, a lower tank valve 604, a dump valve 606, a strainer 608, a bypass valve 610, and a flow meter 612.

FIG. 6 illustrates the various fluid system assembly components. FIG. 7 illustrates one example of how the fluid tank 108, fluid piping system 110, and fluid pump 112 can mount onto the base frame 122 and motor frame 124. More specifically the fluid tank 108 can mount near a front of the base frame 122 with a first side facing forward and a second side facing backward, the fluid piping system 110 can mount to the base frame 122 and the motor frame 124, and the fluid pump 112 can attach to a fluid pump belt 902 that is attached to the engine 102. Generally, the fluid tank 108 stores the fluid, and the fluid pump 112 is responsible for pumping fluid through the fluid piping system 110 from the fluid tank 108 to the nozzle.

As illustrated in FIG. 8, the engine 102 and fluid tank 108 can be mounted on the base frame 122 with a first side of the fluid tank 108 facing forward and a second side of the fluid tank 108 facing backward toward a first side of the engine 102. Further, the engine 102 and fluid tank 108 can be in line from front to back on the base frame 122. However, in some embodiments, the fluid tank 108 can be mounted in front of the engine 102, wherein, instead of a side of the fluid tank 108 facing the engine 102, the back of the fluid tank 108 faces the back of the engine 102.

In other embodiments, the fluid dispersion machinery can include two or more fluid tanks 108 that are mounted on a plurality of the sides of the engine 102. For example, three fluid tanks 108 may be mounted on the base frame 122 and positioned on the left side, front, and right side of the engine 102. This layout enables an individual to transition use from one fluid tank 108 to another without unloading a first fluid tank and loading a second.

FIG. 8 further illustrates how the engine 102 is positioned relative to the fluid piping system 110. This positioning is important because the engine 102 powers the fluid pump 112. As illustrated in FIG. 9, a fluid pump belt 902 attaches to the engine 102 and the fluid pump 112. When the engine 102 is powered, it rotates the fluid pump belt 902, which, in turn, powers the fluid pump 112.

Figure 10:
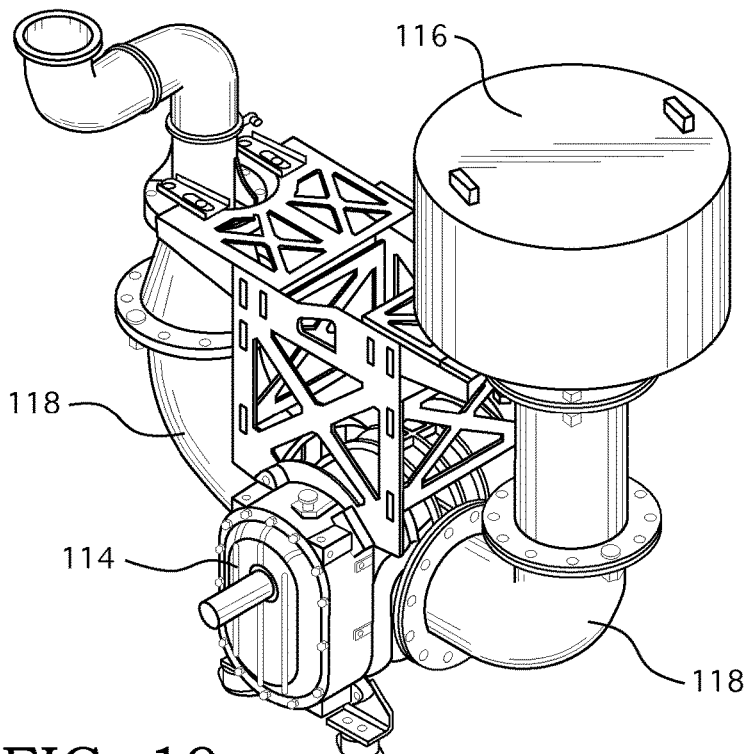
FIG. 10 illustrates an air compression assembly of the fluid dispersion machinery according to one embodiment of the disclosed invention.

In some embodiments, a portion of the support machinery includes an air compression assembly comprised of an air compressor 114, an air compressor intake and silencer 116, a first set of air ducting 118 that connects the air compressor 114 to the air compressor intake and silencer 116, and a second set of air ducting 118 that connects the air compressor 114 to the nozzle. FIG. 10 illustrates the various components of the air compression assembly.

Figure 11:
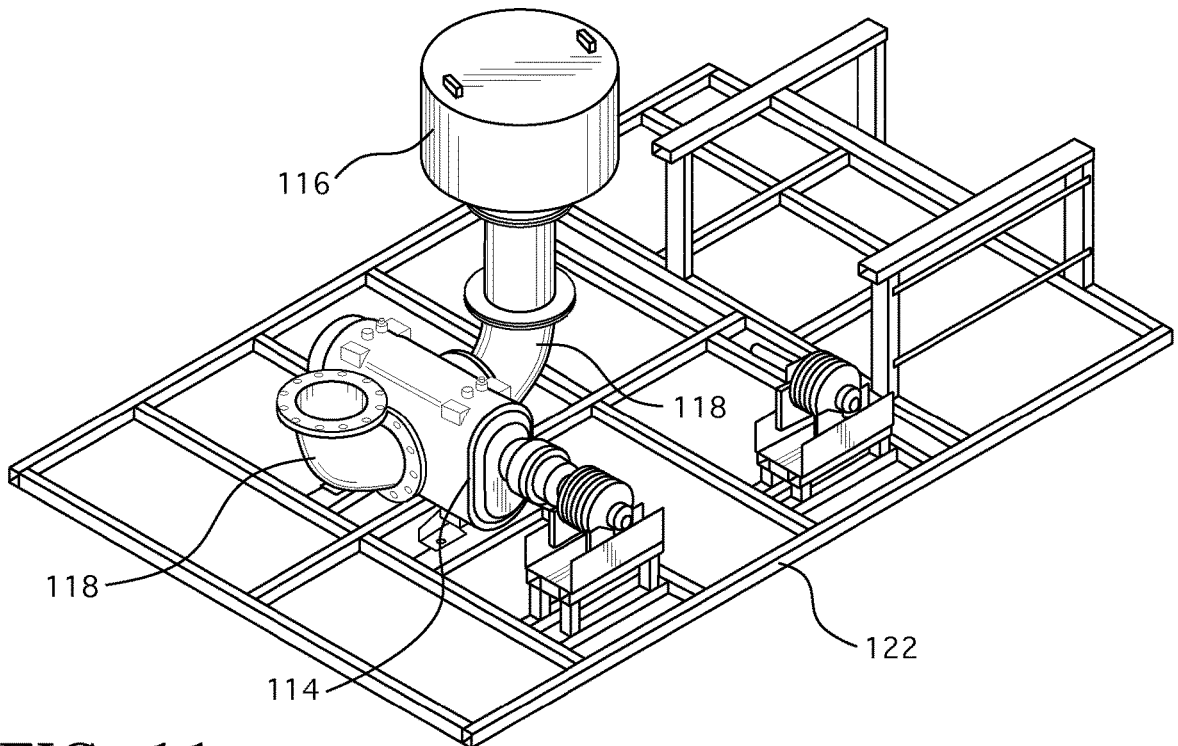
FIG. 11 illustrates the air compression assembly of FIG. 10 mounted onto the base frame and motor frame of the fluid dispersion machinery according to one embodiment of the disclosed invention.

FIG. 11 illustrates one example of how the air compressor 114, air compressor intake and silencer 116, and air ducting 118 can mount onto the base frame 122. More specifically, the air compressor 114 can mount near a back of the base frame 122, the air compressor intake and silencer 116 can mount on the first set of air ducting 118 that attaches to a first side of the air compressor 114 and faces forward toward a second side of the engine 102, and the second set of air ducting 118 that connects to the nozzle can attach to a second side of the air compressor 114 and can face backward.

As illustrated in FIGS. 1 and 2, the sides of the engine assembly and the air compression assembly can be mounted on the base frame 122 and motor frame 124 so that their sides are facing each other. However, in a preferred embodiment, the engine assembly and the air compression assembly are mounted in line so that the front of the engine 102 connects to the back of the air compressor 114. When the engine 102 and air compressor 114 are mounted side by side, as illustrated in FIGS. 1 and 2, a belt is needed to transfer power from the engine 102 to the air compressor 114 whereas, when the engine 102 and air compressor 114 are mounted in line, the engine 102 can directly connect to, and transfer power to, the air compressor 114.

As described above, the vehicle-mounted fluid dispersion machinery can be controlled by an in-cab control system, illustrated in FIG. 13. In some embodiments, the in-cab control system can start the engine 102, the fluid pump 112, and the air compressor 114. Additionally, it can increase and decrease the engine RPMs, can track fuel levels, fluid levels, water temperature, and can turn work lights on and off, among other tasks.

What is claimed is:

1. A method for object-customized dispersal of fluid particles, the method comprising:
    selecting an object to which the fluid particles are to be applied;
    tracking air temperature near a ground surface and near a top of the object;
    waiting for an object-specific application condition that includes a predetermined temperature difference between the air temperature at the top of the object and the air temperature near the ground surface and, in response to the predetermined temperature difference being reached, initiating the object-customized dispersal of the fluid particles, including:
    using a fluid pump to pressurize a fluid;
    using an air compressor to pressurize air particles;
    combining the pressurized fluid and the pressurized air particles in a nozzle, wherein the combination of pressurized fluid, pressurized air particles, and further air acceleration provided by the nozzle enables creation of a cloud of near-monodispersed droplets that are released from an end of the nozzle;
    aiming the nozzle so the near-monodispersed droplets are released upwind from the object and directed toward the top of the object;
    wherein:
        the object-specific application condition includes a nighttime air inversion as represented by the predetermined temperature difference; and
        during the object-specific application condition the near-monodispersed droplets are pulled down onto a surface of the object.

2. The method of claim 1, wherein the object is a plant.

3. The method of claim 2, wherein the fluid is a herbicide.

4. The method of claim 2, wherein the nozzle is aimed above the top of the object.

5. The method of claim 1, wherein the object is livestock equipment and premises and the fluid is a disinfectant.

6. The method of claim 1, wherein the near-monodispersed droplets can travel up to two miles away from the nozzle.

7. The method of claim 1, wherein the near monodispersed droplets have diameters between 5 and 150 microns.

8. The method of claim 1, wherein the predetermined temperature difference is one degree Fahrenheit and the temperature of air at the top of the object is one degree warmer than the temperature of air near the ground surface.

9. The method of claim 1, wherein the method is limited to implementation when the wind speed is equal to or less than 9 miles per hour.

10. The method of claim 1, wherein the fluid is approximately 10 percent water.

11. The method of claim 1, wherein the nozzle is a supersonic, adjustable, dual-contour nozzle.

12. The method of claim 11, wherein, the fluid hits various barriers within the nozzle and breaks into the near-monodispersed droplets.

13. The method of claim 12, wherein the accelerated air pushes the near-mondispersed droplets away from the nozzle.

14. The method of claim 1, further comprising:
    providing fluid dispersion machinery including:
        an engine;
        a radiator;
        a fuel tank;
        a fluid tank;
        a fluid piping system;
        a fluid pump powered by a fluid pump belt attached to the engine;
        an air compressor;
        an air compression intake and silencer;
        air ducting fluidly coupled to the nozzle;
        a clutch; and
        an in-cab control system that controls the fluid dispersion machinery;
    wherein the fluid dispersion machinery is attached to a base frame, and the engine is attached to a motor frame that is mounted to the base frame.

15. The method of claim 14, wherein the fluid dispersion machinery is provided such that:
    the fluid tank is mounted near a front of the base frame with a first side facing forward and a second side facing backward;
    the air compressor is mounted near a back of the base frame;
    the motor frame is mounted on the base frame;
    the engine is mounted on the motor frame, is located between the fluid tank and the air compressor, and has a first side facing the second side of the fluid tank and a second side facing the air compressor;

the fluid piping system is mounted to the base frame and the motor frame;

the motor frame has a horizontal portion and a vertical portion;

the horizontal portion of the motor frame is mounted to a central portion of the base frame;

the vertical portion of the motor frame is mounted to a right side of the base frame;

the engine is mounted to the horizontal portion of the motor frame; and the radiator is mounted to the vertical portion of the motor frame.

16. A method for dispersing disinfectant onto a target structure, the dispersal being customized to the target structure, the method comprising:

selecting the target structure to which the disinfectant is to be applied;

tracking air temperature near a ground surface and near a top of the target structure;

waiting for a target structure specific application condition that includes a predetermined temperature difference between the air temperature at the top of the target structure and the air temperature near the ground surface and, in response to the predetermined temperature difference being reached, initiating the target-structure customized dispersal of the disinfectant, including:

using a fluid pump to pressurize a fluid disinfectant;

using an air compressor to pressurize air particles;

combining the pressurized fluid disinfectant and the pressurized air particles in a nozzle, wherein the combination of pressurized fluid disinfectant, pressurized air particles, and further air acceleration provided by the nozzle forms a cloud of near-monodispersed droplets that are released from an end of the nozzle;

aiming the nozzle so the near-monodispersed droplets are released upwind from the target structure and directed toward the top of the target structure;

wherein:

the target structure specific application condition includes a nighttime air inversion as represented by the predetermined temperature difference; and during the target structure specific application condition the near-monodispersed droplets are pulled down onto a surface of the target structure.

17. The method of claim 16, further comprising: aiming the nozzle above the top of the target structure.

18. The method of claim 16, further comprising: in the nozzle, breaking the fluid disinfectant into the near-monodispersed droplets by causing the fluid disinfectant to hit various barriers.

19. The method of claim 16, wherein the near monodispersed droplets have diameters between 5 and 150 microns.

* * * * *